(12) United States Patent
Andblom et al.

(10) Patent No.: US 11,908,579 B2
(45) Date of Patent: Feb. 20, 2024

(54) METHOD AND SYSTEM FOR DETERMINING A SPECIFIC TEST TO BE PERFORMED IN ORDER TO DETERMINE THE BIOLOGICAL CONDITION OF A BIOLOGICAL SUBJECT

(71) Applicant: BraineHealth AB, Norrtälje (SE)

(72) Inventors: Mikael Andblom, Stockholm (SE); Roger Svensson, Hallstavik (SE)

(73) Assignee: BRAINEHEALTH AB, Norrtälje (SE)

(*) Notice: Subject to any disclaimer, the term of this patent is extended or adjusted under 35 U.S.C. 154(b) by 480 days.

(21) Appl. No.: 17/290,211

(22) PCT Filed: Oct. 18, 2019

(86) PCT No.: PCT/SE2019/051023
§ 371 (c)(1),
(2) Date: Apr. 29, 2021

(87) PCT Pub. No.: WO2020/091649
PCT Pub. Date: May 7, 2020

(65) Prior Publication Data
US 2022/0020493 A1    Jan. 20, 2022

(30) Foreign Application Priority Data
Nov. 1, 2018   (SE) .................. 1851364-8

(51) Int. Cl.
*G16H 50/20* (2018.01)
*A61B 5/00* (2006.01)

(52) U.S. Cl.
CPC .......... *G16H 50/20* (2018.01); *A61B 5/7264* (2013.01); *A61B 5/7275* (2013.01); *A61B 2503/40* (2013.01)

(58) Field of Classification Search
CPC ... A61B 5/7264; A61B 5/7267; A61B 5/7275; A61B 5/01; A61B 5/021; A61B 2503/40;
(Continued)

(56) References Cited

U.S. PATENT DOCUMENTS

| 6,029,138 A | 2/2000 | Khorasani et al. |
| 11,705,230 B1* | 7/2023 | Jain ................. G16H 10/60 705/3 |

(Continued)

FOREIGN PATENT DOCUMENTS

| GB | 2555381 | 5/2018 |
| WO | 2018/128927 | 7/2018 |

OTHER PUBLICATIONS

International Search Report for PCT/SE2019/051023 dated Dec. 6, 2019, 6 pages.
(Continued)

*Primary Examiner* — An H Do
(74) *Attorney, Agent, or Firm* — NIXON & VANDERHYE

(57) ABSTRACT

A computer-implemented method for determining a biological test to be performed on a biological subject in order to determine the biological condition of the biological subject, and a corresponding system and computer program. Disclosed technology creates a basis representation for a set of biological symptoms, reads input data obtained from a biological subject whose biological condition is to be determined, generates a representation of the input data in the created basis representation, applies a predictive model to the representation of the input data in order to obtain a probability distribution that parameters included in the input data corresponds to a specific biological condition.

16 Claims, 4 Drawing Sheets

(58) Field of Classification Search
CPC .... A61B 5/14532; G06N 3/084; G16H 50/20; G16H 50/30; Y02A 90/10
See application file for complete search history.

(56) References Cited

U.S. PATENT DOCUMENTS

| | | |
|---|---|---|
| 2001/0023419 A1 | 9/2001 | Lapointe et al. |
| 2005/0020903 A1 | 1/2005 | Krishnan et al. |
| 2016/0321414 A1 | 11/2016 | Salganicoff et al. |
| 2018/0107798 A1 | 4/2018 | Hu |
| 2020/0279622 A1* | 9/2020 | Heywood .............. G16H 15/00 |

OTHER PUBLICATIONS

Written Opinion of the ISA for PCT/SE2019/051023 dated Dec. 6, 2019, 9 pages.
Riches et al., "The Effectiveness of Electronic Differential Diagnoses (DDX) Generators: A Systematic Review and Meta-Analysis", PLOS One, Mar. 2016, vol. 11, pp. 1-26 (26 total pages).

* cited by examiner

METHOD AND SYSTEM FOR DETERMINING A SPECIFIC TEST TO BE PERFORMED IN ORDER TO DETERMINE THE BIOLOGICAL CONDITION OF A BIOLOGICAL SUBJECT

CROSS-REFERENCE TO RELATED APPLICATIONS

This application is the U.S. national phase of International Application No. PCT/SE2019/051023 filed Oct. 18, 2019 which designated the U.S. and claims priority to SE 1851364-8 filed Nov. 1, 2018, the entire contents of each of which are hereby incorporated by reference.

TECHNICAL FIELD

The proposed technology generally relates to a computer-implemented method for determining a biological test to be performed on a biological subject in order to determine the biological condition of the biological subject. The proposed technology also relates to a system configured to determine a biological test to be performed on a biological subject in order to determine the biological condition of the biological subject.

BACKGROUND

The use of neural networks to establish e.g., correlations between input data and collected empirical data in complex systems is a rapidly improving field. With the help of well-built data bases associating specific characteristics of the input data with established states corresponding to the input data a number of systems has been developed that is able to train a neural network based on the data bases and obtain outputs from the same that can facilitate further analysis of the input data. One particular example of a complex system where the use of neural networks has been shown to be immensely useful is a biological system. Biological systems, such as a mammal body, are overwhelmingly complicated and even small perturbations of minor subsets of the system may have substantial effect on the overall biological condition of the body. This is of course the main reason that e.g., the art of diagnosing a patient is so hard. Minor symptoms that can be easily overlooked may in fact be the most relevant ones. The development of neural networks and the training of the same on large sets of data has been shown to provide novel correlations that can be beneficial when determining the biological condition of a biological system such as a mammal body.

In general it is a well-known procedure to use trained neural networks in order to suggest a plausible diagnosis based on certain specified symptoms, e.g., based on measured quantities that are fed into a trained neural network. The trained network is able to correlate the input data, e.g., a set of symptoms, with specific output data, e.g., specific diagnoses. A system that is able to find such correlations may be very beneficial for determining the biological condition of a biological subject such as a mammal body. Due to the fact that a mammal body is so complicated there is a huge amount of possible causes that can be the underlying reason behind a specific symptom that is experienced by the biological subject. There may for example be several different complex diseases or bodily dysfunctions that may all be the root cause to the symptom. Some of the diseases or dysfunctions may be very rare and they may in addition generate similar symptoms. There is therefore a great amount of information to consider when performing differential diagnostics. Relevant information may for example be the medical history of the patient, current symptoms, measurements, lab results, x-ray images etc. A system that is able to process such information could be very beneficial when analyzing a biological subject such as a mammal body.

Currently there exists several systems that are developed to provide support when analyzing complex biological systems. Their practical usefulness and efficiency has however been questioned, see e.g., "The effectiveness of electronic differential diagnoses generators: A systematic review and meta-analysis". N. Riches et al. PLOS ONE, vol. 11, pp 1-26, 03-2016.

One particular aspect that is common when complex biological systems are analyzed by using neural networks or machine learning is that the end result can be significantly improved if a lot of initial data is provided to the system. If a lot of measurements are performed on a biological system, the initial knowledge of the system will get increased. This will in turn improve the end result. There is therefore a lot of incentives to provide as much information as possible about the system before applying the machine learning functionality. This may however also be a drawback since any measurement performed are demanding resources and costs money. The tests or measurements may also be detrimental to the biological system under study, e.g., a patient that is subjected to a lot of possibly meaningless tests or a cell subjected to possibly cell damaging tests.

In order to obtain a more efficient low-costing analysis support problems like these has to be addressed. There is therefore a clear need within the art to further develop effective tools that can be used when analyzing complex biological systems. The proposed technology aims to provide tools or mechanisms that can be used to support the analysis of complex biological systems as well as enabling a reduction of the number of measurements/test that needs to be conducted. It aims in particular to provide mechanisms that will enable a user to determine which future measurement(s) that are to be performed in order to determine the state or condition of a biological subject or system.

SUMMARY

It is an object to provide a computer-implemented method and a corresponding system that can be used to determine a biological test to be performed on a biological subject in order to determine the biological condition of the biological subject.

It is another object to provide a computer-implemented method and a corresponding system that can be used to determine a biological test to be performed on a biological subject such as a patient in order to determine a disease or a dysfunctionality experienced by a patient.

It is still another object to provide a computer program that can be used to determine a biological test to be performed on a biological subject such as a patient in order to determine a disease or a dysfunctionality experienced by a patient.

These and other objects are met by embodiments of the proposed technology.

According to a first aspect, there is provided a computer-implemented method for determining a biological test to be performed on a biological subject in order to determine the biological condition of the biological subject. The computer-implemented method comprises creating a basis representation s of a set of biological symptoms. The computer-implemented method also comprises reading input data obtained from a biological subject whose biological condition is to be determined. The input data comprising parameters quantifying a number of biological symptom $s_i$, $1 \le i \le N$, associated with the biological subject. The computer-implemented method also comprises generating a representation s' of the input data in the created basis representation s. The computer-implemented method also comprises applying a predictive model M(s) to the representation s' of the input data in order to obtain a probability distribution d that yields the probabilities $d_i$ that the parameters comprised in the input data corresponds to a specific biological condition $y_j$. The predictive model M(s) being determined by applying a neural network on a set of data associating the biological symptoms $s_i$ with specific biological conditions $y_j$. The set of data comprises collected empirical data that associates the biological symptoms $s_i$ with a determined biological condition $y_j$. The computer-implemented method also comprises performing a first optimization of a probability $d_i$ comprised in the probability distribution d with respect to a test indicating parameter x1, the test indicating parameter $x_1$ being associated with a biological symptom $s_k$ different from the biological symptoms $s_i$, and being represented in the basis representation s, in order to obtain a first optimized probability value $d_i^*$. The computer-implemented method also comprises performing at least one additional optimization of the obtained probability $d_i$ comprised in the probability distribution d with respect to a different test indicating parameter $x_2$, the test indicating parameter $x_2$ being associated with yet another additional biological symptom $s_m$ different from the additional biological symptom $s_k$ and the biological symptom $s_i$, and being represented in the basis representation s, in order to obtain at least one additional optimized probability value $d_i^{**}$. The computer-implemented method also comprises determining a biological test to be conducted on the biological subject based on a comparison between the obtained optimized probability values $d_i^*$, $d_i^{**}$.

According to a second aspect there is provided a system configured to determining a biological test to be performed on a biological subject in order to determine the biological condition of the biological subject. The system is configured to create a basis representation s for a set of biological symptoms. The system is also configured to read input data obtained from a biological subject whose biological condition is to be determined, the input data comprising parameters quantifying a number of biological symptom $s_i$, $1 \le i \le N$ associated with the biological subject. The system is also configured to generate a representation s' of the input data in the created basis representation s. The system is also configured to apply a predictive model M(s) to the representation s' of the input data in order to obtain a probability distribution d that yields the probabilities $d_i$ that the parameters comprised in the input data corresponds to a specific biological condition $y_j$, the predictive model M(s) being determined by applying a neural network on a set of data, the set of data comprising collected empirical data associating the biological symptoms $s_i$ with a determined biological condition $y_j$. The system is also configured to perform a first optimization of a probability $d_i$ comprised in the probability distribution d with respect to a test indicating parameter $x_1$, the test indicating parameter $x_1$ being associated with a biological symptom $s_k$ different from the biological symptoms $s_i$, and being represented in the basis representation s, in order to obtain a first optimized probability value $d_i^*$. The system is also configured to perform at least one additional optimization of the obtained probability $d_i$ comprised in the probability distribution d with respect to a different test indicating parameter $x_2$, the test indicating parameter $x_2$ being associated with yet another additional biological symptom $s_m$ different from the additional biological symptom $s_k$ and the biological symptom $s_i$, and being represented in the basis representation s, in order to obtain at least one additional optimized probability value $d_i^{**}$. The system is also configured to determine a biological test to be conducted on the biological subject based on a comparison between the obtained optimized probability values $d_i^*$, $d_i^{**}$.

According to a third aspect there is provided a computer program that comprises instructions, which when executed by at least one processor, cause the processor(s) to:

create a basis representation s for a set of biological symptoms;

read input data obtained from a biological subject whose biological condition is to be determined, the input data comprising parameters quantifying a number of biological symptom si, $1 \le i \le N$, associated with the biological subject;

generate a representation s' of the input data in the created basis representation s;

read a probability distribution d that yields the probabilities di that the parameters comprised in the input data corresponds to a specific biological condition yj, the probability distribution d being obtained by applying a predictive model M(s) to the representation s' of the input data, the predictive model M(s) being determined by applying a neural network on a set of data, the set of data comprising collected empirical data associating the biological symptoms si with a determined biological condition yj;

perform a first optimization of a probability di comprised in the probability distribution d with respect to a test indicating parameter x1, the test indicating parameter x1 being associated with a biological symptom sk different from the biological symptoms si, and being represented in the basis representation s, in order to obtain a first optimized probability value di*;

perform at least one additional optimization of the obtained probability di comprised in the probability distribution d with respect to a different test indicating parameter x2, the test indicating parameter x2 being associated with yet another additional biological symptom sm different from the additional biological symptom sk and the biological symptom si, and being represented in the basis representation s, in order to obtain at least one additional optimized probability value di**; and output a specific biological test to be conducted on the biological subject, the biological test being determined based on a comparison between the obtained optimized probability values di*, di**.

Embodiments of the proposed technology provides mechanisms that will enable a user to efficiently design upcoming measurements procedures in order to obtain a better understanding of the complex biological system. The proposed mechanisms will enable a reduction of the number of unnecessarily conducted tests. This will in turn reduce the strain on the biological subject and reduce the costs associated with the analysis. Other advantages will be appreciated when reading the detailed description.

BRIEF DESCRIPTION OF THE DRAWINGS

The embodiments, together with further objects and advantages thereof, may best be understood by making reference to the following description taken together with the accompanying drawings, in which.

DETAILED DESCRIPTION

Figure 1:
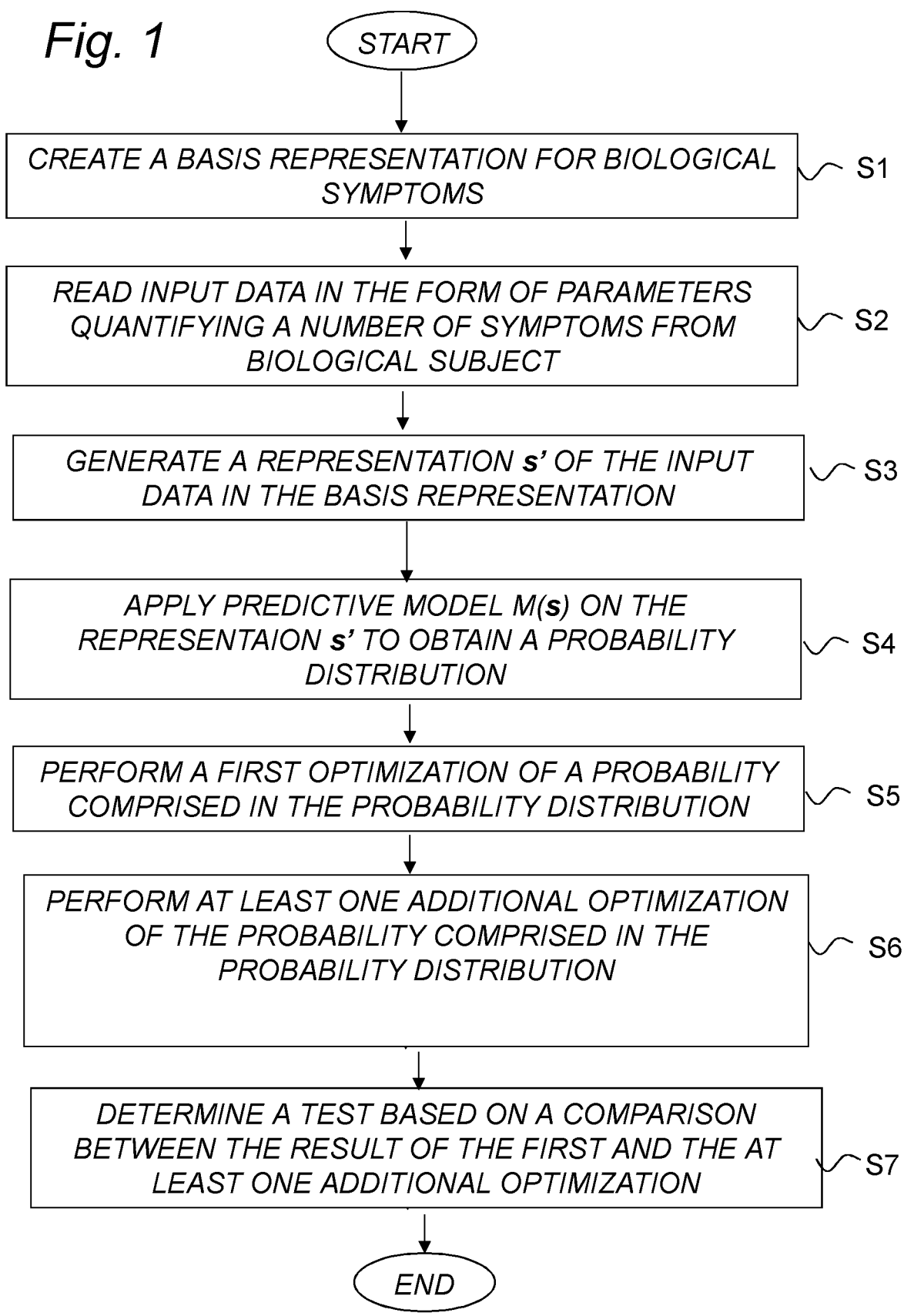
FIG. 1 is a schematic illustration of a flow diagram illustrating a method according to the proposed technology.

Throughout the drawings, the same reference designations are used for similar or corresponding elements.

Generally, all terms used herein are to be interpreted according to their ordinary meaning in the relevant technical field, unless a different meaning is clearly given and/or is implied from the context in which it is used. All references to a/an/the element, apparatus, component, means, step, etc. are to be interpreted openly as referring to at least one instance of the element, apparatus, component, means, step, etc., unless explicitly stated otherwise. The steps of any methods disclosed herein do not have to be performed in the exact order disclosed, unless a step is explicitly described as following or preceding another step and/or where it is implicit that a step must follow or precede another step. Any feature of any of the embodiments disclosed herein may be applied to any other embodiment, wherever appropriate. Likewise, any advantage of any of the embodiments may apply to any other embodiments, and vice versa. Other objectives, features and advantages of the enclosed embodiments will be apparent from the following description.

For a better understanding of the proposed technology, it may be useful to begin with an overview of the technical problem addressed by the proposed technology. To this end we will describe the overall environment and purpose of the proposed technology in a specific setting. This specific setting should however not be seen as limiting for the proposed technology. The proposed technology aims to provide mechanisms that will enable a user to determine a specific biological test to be performed on a biological subject in order to determine the biological condition of the biological subject. The biological test may for example be a diagnostic test that is to be performed on a biological subject in the form of a patient in order to determine whether the patient is suffering from a biological condition in the form of a specific disease or a specific dysfunctionality. The proposed technology will be described below in this specific setting. It should however be noted that the technology of the present disclosure can be equally well applied to other biological systems or subjects, such as e.g., a cell. We will in what follows always refer to a specific biological state as a biological symptom regardless of the exact nature of the biological state. We may for example color a cell with a particular color, say red, and refer to the redness of the cell as the observed biological symptom of the cell. The term biological symptom should therefore not be construed as meaning merely the biological state of a patient, it could equally well mean the observed consequence of a specific biological action, such as the coloring of the cell above.

As referred to herein a biological condition may be referred to as a disease or some other bodily dysfunction of a biological subject in the form of a patient. The biological condition may however equally well refer to specific characteristics of some other biological system such as e.g., a cell. It may for example refer to the reactiveness of a specific cell. Regardless of the actual biological system that is to be analyzed using the proposed technology, the biological conditions of the system will often cause observable and quantifiably symptoms or other measurable abnormalities. The observable and quantifiable symptoms can, in the case where the biological condition is a disease, for instance be pain, coughing or fever while other measurable abnormalities can be e.g. x-ray images, blood sugar levels or blood pressure. In other words, we have the causal relationship:

$$\text{biological condition} \rightarrow \text{obtainable abnormal data relating to biological symptoms displayed by the system,} \quad (1)$$

or, in the specific case;

$$\text{disease} \rightarrow \text{obtainable abnormal patient data.} \quad (2)$$

Regarding the second bullet above, it should be noted that the medical personnel essentially works the other way around. They gather data about the patient and other relevant information in order to try to estimate the most probable diagnosis for the underlying disease. Relevant information to consider in these scenarios can be things such as location, time of season or gender. Some diseases are location based like malaria while some diseases are common during e.g., the winter season such as the influenza. The medical personnel thus performs the following task:

$$\text{patient data and other relevant information} \rightarrow \text{diagnosis.}$$

The proposed technology aims to provide a computer-implemented support for analyzing complex biological systems. A general method that may be used to attack problems (1) and (2) above is to utilize a predictive model M in order to generate correlations that associates specific biological symptoms with an overarching biological condition. The proposed technology obtains the predictive model by applying a machine learning tool, e.g., a neural network, to a set of data that associates biological symptoms with specific biological conditions. The set of data comprises collected empirical data that is able to associate a specific biological symptom, or a set of symptoms, with a determined biological condition. The data set may for example comprise a data base with a set of biological conditions, each being associated with specific characterizing symptoms. Having trained the neural network it will be possible to feed the network with input data, usually in the form of parametrized quantifiers of specific biological symptoms, more on that later, in order to obtain a probability distribution d from the network. The probability distribution d will, according to the proposed technology, yield the different probabilities that the input data, e.g., the parameters quantifying the symptom, corresponds to, or are caused by a specific biological condition, e.g., a disease or a dysfunction. Having obtained the probability distribution the proposed technology aims to provide a mechanism whereby it will be possible to suggest additional biological tests, e.g., lab tests, x-ray measurements or other measurements that should be performed in order to either increase or decrease the confidence that a certain biological condition is the cause of the biological symptoms. Generated suggestions of such additional test may prove very beneficial in cases where several conditions may underlie the biological symptoms. The outcome of the suggested additional tests may for example increase the confidence that a particular condition is the cause sufficiently enough so that e.g., a patient can be diagnosed and conversely they can decrease the confidence sufficiently so that another condition or diagnosis can be ruled out.

Having described a birds-eye view of the proposed technology, in what follows we will describe a number of embodiments and examples of the same. Some of the embodiments contemplated herein will be described more fully with reference to the accompanying drawings. Other embodiments, however, are contained within the scope of the subject matter disclosed herein, the disclosed subject matter should not be construed as limited to only the embodiments set forth herein; rather, these embodiments are provided by way of example to convey the scope of the subject matter to those skilled in the art.

FIG. 1 is a schematic flow diagram illustrating an example of a computer-implemented method for determining a biological test to be performed on a biological subject in order to determine the biological condition of the biological subject. The computer-implemented method comprises creating S1 a basis representation s of a set of biological symptoms. The computer-implemented method also comprises reading S2 input data obtained from a biological subject whose biological condition is to be determined. The input data comprising parameters quantifying a number of biological symptom $s_i$, $1 \leq i \leq N$, associated with the biological subject. The computer-implemented method also comprises generating S3 a representation s' of the input data in the created basis representation s. The computer-implemented method also comprises applying S4 a predictive model M(s) to the representation s' of the input data in order to obtain a probability distribution d that yields the probabilities $d_i$ that the parameters comprised in the input data corresponds to a specific biological condition $y_i$. The predictive model M(s) being determined by applying a neural network on a set of data associating the biological symptoms $s_i$ with specific biological conditions $y_j$. The set of data comprises collected empirical data that associates the biological symptoms $s_i$ with a determined biological condition $y_j$. The computer-implemented method also comprises performing S5 a first optimization of a probability $d_i$ comprised in the probability distribution d with respect to a test indicating parameter $x_1$, the test indicating parameter $x_1$ being associated with a biological symptom $s_k$ different from the biological symptoms $s_i$, and being represented in the basis representation s, in order to obtain a first optimized probability value $d_i^*$. The computer-implemented method also comprises performing S6 at least one additional optimization of the obtained probability $d_i$ comprised in the probability distribution d with respect to a different test indicating parameter $x_2$, the test indicating parameter $x_2$ being associated with yet another additional biological symptom $s_m$ different from the additional biological symptom $s_k$ and the biological symptom $s_i$, and being represented in the basis representation s, in order to obtain at least one additional optimized probability value $d_i^{**}$. The computer-implemented method also comprises determining S7 a biological test to be conducted on the biological subject based on a comparison between the obtained optimized probability values $d_i^*$, $d_i^{**}$.

The output of the above described method provides a suggestion of a specific biological test that can be used to determine the biological condition of the biological subject that experience the symptoms. Alternatively the suggested method may be used to determine, or provide a suggestion of, a biological test that can be performed in order to increase the confidentiality that the biological symptoms experienced or observed are caused by a specific biological condition.

We will now describe each of the steps S1-S7 of the computer-implemented method in greater detail. We will describe several of the steps by using specific examples, these specific examples are merely used to facilitate the understanding of the proposed technology and any specific representation used to describe them are not to be seen as a limiting feature.

First of all the computer-implemented method comprises the step S1 of creating a basis representation s of a set of biological symptoms. This step will ensure that a representation that can be subjected to the predictive model M(s) is furnished. The basis representation that we denote s should be a computer processing friendly representation. The representation may for example furnish a vector representation where each element of the vector representation, i.e., each vector component, comprises a parameter that quantifies at least some aspect of a biological symptom. We may for example create a vector representation of s where the individual components $s_i$ specifies, in a parametrized fashion, particular aspects of distinct symptoms $s_i$ That is, the symbol $s_i$ denotes a specific vector component in s, as well as a specific symptom. This representation is suitable when the neural network can be represented by means of a matrix representation. A concrete example will now be provided that should explain the creation of a basis representation s. Suppose that we have two distinct symptoms $s_1$ and $s_2$. $s_1$ may for example label the temperature of a patient experiencing fever and $s_2$ may instead refer to headache. A basis representation using vectors can in this particular example be written:

$$s=[s_1,s_2]^+,$$

where the plus sign denotes the vector transpose.

The vector basis representation above is however merely one particular representation of many. It will be possible to represent the basis in a number of different ways, e.g., in the form of arrays, matrices, tensors, general lists or dictionaries, or as certain collection of data, all in accordance with the representation given to the neural network. The important thing is that the representation furnishes an object where each component is associated with a specific biological symptom and where the object can be subjected to a predictive model that is determined by applying a neural network on a set of data that associates the biological symptoms $s_i$ with specific biological conditions $y_j$. The step S1 will act to create a basis representation s into which input data can be fed.

We now provide a brief interlude in order to describe some aspects of the notation used. Note in particular that the biological symptoms are denoted $s_i$, while the biological conditions are denoted $y_j$. The difference in index used, i.e., i and j, are intended to clarify that there may be a difference in the number of biological symptoms and the number of biological conditions. The index i used for the biological symptoms may for example run between 1 and N, while the index j used for the biological conditions may run between 1 and M, where N might be a larger than M. This takes into consideration the fact that a specific biological condition, e.g., a disease, may be associated with several distinct biological symptoms. So when it is stated biological symptom $s_i$ it is intended either a set of biological symptoms where the index i for example run between 1 and n, or a single biological symptom where the index i takes a specific value, e.g., i=4.

Having created such a basis representation the method may now read, in step S2, input data that is obtained from the biological subject, e.g., the patient whose biological condition is to be determined. The input data may in certain embodiments relate to measured values, i.e., temperature, blood pressure, blood values or other measurable quantities relevant for the biological condition of the biological subject. The input data may also comprise information obtained from other objective biological tests, such as e.g., lab-tests or x-ray images. The input data may in other embodiments also comprise subjective estimations of some experienced biological symptoms, e.g., an estimation of pain levels, level of nausea, level of dizziness etc. The input data should be quantified in order to obtain parameters that quantifies a number of distinct biological symptom $s_i$, $1 \leq i \leq N$, that is associated with the biological subject. The input data may for example comprise one parameter that quantifies the temperature of the subject and additional parameters that quantifies some other symptom(s) that is either experienced by the subject or is measured or observed. The parametrization could in particular cases be directly associated with the actual observable or measurable quantity, e.g., a measured body temperature given in suitable units, e.g., in Celsius or Kelvin. The parametrization may also be strictly binary, for example writing 1 for an observed biological symptom, e.g., the cell has the color red—the patient experiences headache, and 0 for the complementary aspect of the symptom, e.g., the cell does not have the color red—the patient does not experience headache. A particular input data comprising the temperature T of the biological subject may thus be represented as, $s=[T, 1]^+$. This may for example be used to represent two distinct symptoms $s_1$ and $s_2$ where $s_1$ represents fever and $s_2$ represents headache, i.e., 1 provides a binary parameter that the subject experience headache. The parametrisation of the input data may beneficially also be subjected to scaling so that each component are given numerical values that have similar orders of magnitude. One may in the case with T=38.2 C for example scale $s=[T, 1]^+$ from above in order to obtain $s=[3, 1]^+$, where the temperature has been scaled so the interval 37.0-37.5 is parametrised by 1 and the interval 37.6-38.0 is parametrised by 2 and 38.1 and upwards are parametrised by 3. The parameters are now of similar order of magnitude. Such scaling may yield more stable processes when the input data is subjected to a predictive model. There are of course a lot of ways to design a scheme for scaling the parameters, the particular scheme and scaling that is used should be based on the actual application of the method.

The section above also provides specific examples of how the step S3 in the computer-implemented method of the proposed technology generates a representation s' of the input data in the created basis representation s. In the examples above the basis representation was furnished by the vector representation and the input data was parametrised and inserted into the basis representation in order to generate a representation s' of the input data in the created basis representation s.

Before proceeding and describing the step S4 of applying a predictive model to the generated representation s' of the input data we will briefly recapitulate steps S1-S3 in a particularly simple example. Assume that we have a biological subject on which we may obtain three quantifiable measures of biological symptoms $s'_i$, where the index i runs from 1 to 3. Assume further that we have created a basis representation s using a N-dimensional basis representation $s=[s_1, s_2, s_3, \ldots s_N]^+$. The input data in the computer implemented method comprises parametrizations of the measured or obtained values relating to the biological symptoms $s'_i$. If, for example, $s'_1=7$ in some suitable unit, $s'_2=3$ in some suitable unit and $s'_3=4$ in some suitable unit it is possible to represent the input data in the created basis representation as:

$$s'=[7,3,4,0 \ldots 0]^+$$

This particular representation, obtained by applying steps S1-S3, are to be subjected to a predictive model M(s) in step S4. That is, a predictive model M(s) are to be applied to the generated representation s'. The outcome or output of this particular step is a probability distribution d that yields the probabilities that a specific set of biological symptoms corresponds to, or are caused by, a particular set of biological conditions. The probability distribution d will be provided in the same representation as the basis representation that was used, but it may be lower dimensional since the number of biological conditions may be a lot smaller than the number of biological symptoms. In the example provided above the probability distribution may for example be given by:

$$d=[d_1,d_2,d_3 \ldots d_M]^+$$

Where M might be smaller than N. Note that if an N-dimensional representation of d is used there is a high probability that a large number of the components $d_i$, which gives the probabilities for corresponding biological conditions are zero. It is thus possible to incorporate a step of reducing the dimensionality of the probability distribution d, e.g., reducing it to a number of plausible biological conditions by providing a cut-off where specific probabilities $d_i$ are set to zero if they are smaller than a set number. It is also possible to reduce the dimensionality of the probability distribution ahead of applying the predictive model, e.g., by singling out specific plausible conditions that underlies the biological symptoms given in the representation s'.

The purpose of the predictive model M(s) is to generate the probability distribution d. The predictive model M(s) are obtained by applying a neural network on a set of data associating biological symptoms with specific biological conditions. That is, biological symptoms such as, for example, $s_{i=1}$, $s_{i=4}$, $s_{i=14}$, etc., are associated with a specific biological condition such as, for example $y_{j=2}$. The set of data should preferably comprise collected empirical data that associates the presence of specific biological symptoms with a specific biological condition. The workings of a neural network on a set of data is well-known to the person skilled in the art. A brief explanation of a general neural network and a particular one that can be used in the proposed technology will be provided in the Appendix.

The predictive model M(s) are to be applied on s' representing the input data in order to obtain a probability distribution or, equivalently, a probability vector d in case a vector representation is used, comprising as components the probability that specific biological symptoms $s_i$ is associated with specific biological conditions $y_i$. Formally this can be written as:

$$M(s)=d$$

It should be noted that d, due to the probabilistic interpretation, will comprise elements taking values in the interval [0, 1] and that sums up to unity.

The probability distribution d may, as has been mentioned, be written as a probability vector having components $d_i$, i.e., $d=[d_1, d_2 \ldots d_M]^+$. The probability vector d may be written as $d=p(s')+\alpha$, where $\alpha$ is an error term, which will be ignored in what follows, and p(s') represents P ($d=d_i|s'$). The expression P ($d=y_i|s'$) is the probability that the biological subject has the biological condition $y_i$ given that the biological subject displayed symptoms s'. Each of the components in d above should thus be interpreted as the probability that the biological subject has biological condition $y_i$ given the displayed symptoms s'. To further clarify, consider the case with two possible biological conditions $y_1$ and $y_2$, the conditions may for example specify the state of a cell or a possible diagnosis of a patient, and three biological symptoms represented by s' having vector components $s_1$, $s_2$ and $s_3$. If the predictive model M(s) is applied to the representation s' with the outcome $d_1=0.3$ and $d_2=0.7$, than this should be interpreted to mean that the biological subject displays biological condition $y_1$ with probability 0.7 given the biological symptoms $s_1$, $s_2$ and $s_3$, and biological condition $y_2$ with probability 0.3 given the biological symptoms $s_1$, $s_2$ and $s_3$. At this point in the computer-implemented method, after having applied the predictive model on our representation s', we are provided with a probability distribution or probability vector. The main point of the proposed technology is to provide mechanisms that enables a user to suggest an additional or subsequent biological test to be performed on the biological subject in order to increase or decrease the confidentiality that the suggested biological condition, e.g., the biological condition with highest probability, is the correct one. This particular feature of the proposed technology is obtained by means of steps S5 to S7, which will be described in greater detail below.

We proceed by describing the step S5 of performing a first optimization of a probability $d_i$ comprised in the probability distribution d with respect to a test indicating parameter $x_1$. The test indicating parameter $x_1$ is associated with a biological symptom sk that is different from the biological symptoms $s_i$ that were obtained from the input data, i.e., k≠i. The biological symptom sk can also be represented in the created basis representation s, e.g., as an additional vector component in the vector representation. The test indicating parameter $x_1$ associated with biological symptom $s_k$ is also associated with one, or possibly several, biological tests. The specific biological test(s) associated with the test indicating parameter $x_1$ is inherited from the biological symptom $s_k$. That is, if biological symptom $s_k$ is associated with a specific biological test, then the test indicating parameter $x_1$ is associated with the same test. The optimization of the probability distribution d with respect to the test indicating parameter $x_1$ is performed in order to obtain a first optimized probability value $d_i^*$. The obtained probability value $d_i^*$ provides a numerical measure of the relevance of performing a biological test associated with the test indicating parameter $x_1$.

Step S6 comprises to perform at least one additional optimization of the obtained probability $d_i$ comprised in the probability distribution d, but this time with respect to a different test indicating parameter $x_2$. The test indicating parameter $x_2$ being associated with yet another additional biological symptom $s_m$ that is different from the additional biological symptom sk and also different from the biological symptom(s) $s_i$ obtained from the input data, that is, m≠k and m≠i. The test indicating parameter $x_2$ is also associated with one, or possibly several, biological tests. The specific biological test(s) associated with the test indicating parameter $x_2$ is inherited from the biological symptom $s_m$. That is, if biological symptom $s_m$ is associated with a specific biological test, then the test indicating parameter $x_2$ is associated with the same test. The biological symptom $s_m$ can also be represented in the created basis representation s, e.g., as an additional vector component in the vector representation. The additional optimizations are done in order to obtain at least one additional optimized probability value $d_i^{}$. The obtained probability value $d_i^{}$ provides a numerical measure of the relevance of performing a biological test associated with the test indicating parameter $x_2$.

The optimizations performed in steps S5 and S6 may, depending on the particular application of the proposed technology, be either a maximization or a minimization of the probability $d_i$ comprised in the probability distribution d with respect to the test indicating parameters. Specific examples when it is preferred to use minimization instead of maximization will be provided in what follows. The value(s) obtained from the optimization(s) are not necessarily the global optimum but may instead be a local optimum. It is well-known within the art of optimization that it is very hard to determine whether a given value obtained from an optimization method constitutes a global optimum instead of a local ditto. The proposed technology does not however necessitate the finding of a global optimum so if a local optimum is found by the optimization method it will be possible to select a suitable biological test as a follow up to earlier performed measurements to speed up the ability to determine the biological state of the biological subject.

Having performed a first optimization and at least one additional optimization the output from the method are a set of numerical measures that are associated with a corresponding biological test. These numerical measures are to be compared in step S7 in order to determine a suitable additional test to be performed on the biological subject. To further facilitate the understanding of the method up to and including steps S5 and S6, we will now provide a number of concrete non-limiting examples.

In the following example we consider the case with three possible biological symptoms, $s_1$, $s_2$ and $s_3$. We begin by creating a basis representation in the form of a vector representation. Our vector representation s can be N-dimensional where N is some large number, but in the following s will be five dimensional, i.e., comprising five components. The basis representation can thus be written as:

$$s=[\cdot,\cdot,\cdot,\cdot,\cdot],$$

where the dots are to replaced by parameters associated with specific symptoms. This corresponds to step S1 of the proposed technology.

In the present example one may assume that measurements are done and that these measurements enables a parametrization of the biological symptoms associated with the measurements. We write the parametrizations of the biological symptoms, $s_1$, $s_2$ and $s_3$ as $s_1^P$, $s_2^P$, and $s_3^P$, respectively. These parametrization may be number valued, as in the case of temperature, but they may also be binary, for example writing 1 for an observed biological symptom, e.g., the cell has the color red—the patient experiences headache, and 0 for the complementary aspect of the symptom, e.g., the cell does not have the color red—the patient does not experience headache. Having obtained parametrized version of the measured values it is now possible to represent the input data in the created basis representation as:

$$s'=[s_1^P,s_2^P,s_3^P,0,0]^+$$

This corresponds to step S3 of the proposed technology.

We may now assume that the predictive model M(s) that are to be applied on s' above has been trained on a specific data base that associates symptoms $s_1$, $s_2$ and $s_3$ with biological conditions $y_1$, $y_2$ and $y_3$. The data base may for example be represented as:

TABLE 1

Collected data for Z biological samples

| Sample | $s_1$ | $s_2$ | $s_3$ | $s_4$ | $s_5$ | $y_1$ | $y_2$ | $y_3$ |
|---|---|---|---|---|---|---|---|---|
| 1 | $P_1$ | $P_2$ | $P_3$ | $P_4$ | $P_5$ | 0 | 0 | 1 |
| 2 | $P_6$ | $P_7$ | $P_8$ | $P_9$ | $P_{10}$ | 0 | 1 | 0 |
| . | . | . | . | . | . | . | . | . |
| . | . | . | . | . | . | . | . | . |
| . | . | . | . | . | . | . | . | . |
| z | $P_{Z1}$ | $P_{Z2}$ | $P_{Z3}$ | $P_{Z4}$ | $P_{Z5}$ | 0 | 1 | 0 |

The various P:s in the table above are the actual measured or observed values for a specific sample. Each row in the table corresponds to a sample where a biological condition has been correctly accorded. A specific P, for example P1, could denote a temperature T if sample 1 had that temperature. A data base such as this may be used to determine the model parameters associated with the predictive model M(s), i.e., the weights and the biases. Having obtained the predictive model M(s) it is now possible to evaluate it for any s'.

Assume that M(s) has been applied to s' in step S4 of the proposed technology. The output from this step, i.e., M ($[s_1^P, s_2^P, s_3^P, 0, 0]^+$) can be written as:

$$d=[d_1,d_2,d_3]^+$$

In this example we make, without loss of generality, the further assumption that three biological conditions—$y_1$, $y_2$ and $y_3$—are considered relevant. The components in d are thus the probabilities that the biological symptoms $s_1$, $s_2$ and $s_3$ that were put into the method corresponds to biological conditions $y_1$, $y_2$ and $y_3$, respectively. In this example the optimizations will furthermore comprise maximizations. Having obtained d from step S4, the method will thus proceed and evaluate a first maximization of a specific component $d_i$ comprised in d. The first maximization should be performed with respect to a test indicating parameter $x_1$. The test indicating parameter $x_1$ is associated with yet another additional biological symptom $s_m$ that is different from the additional biological symptom $s_k$ and also different from the biological symptom(s) $s_i$ obtained from the input data, i.e., m≠k and m≠i. The method will also evaluate at least one additional maximization of the obtained probability $d_i$ comprised in the probability distribution d, but this time with respect to a different test indicating parameter $x_k$. This may, in the case where a single additional maximization is done, i.e., $x_k=x_2$ formally be written as:

$$\max d_i([s_1^P,s_2^P,s_3^P,x_1,0]^+) \text{ with respect to } x_1 \quad (*)$$

and $$\max d_i([s_1^P,s_2^P,s_3^P,0,x_2]^+) \text{ with respect to } x_2 \quad (**)$$

Here $x_1$ corresponds to biological symptom $s_4$ and $x_2$ corresponds to biological symptom $s_5$.

Suppose now that we for example want to increase the confidentiality that the biological condition causing the biological symptoms is $y_1$. The probability obtained from the predictive model M (s) that the biological condition $y_1$ is causing the biological symptoms are given by $d_1$. To increase the confidentiality of this prediction we are to supplement the vector s' with an additional component $s_4^P$, parametrized as $x_1$, and perform a first maximization based on this. The additional component $s_4^P$ can be obtained by measuring a specific observable that we denote $T_1$. In addition to this we should also supplement the vector s' with an additional component $s_5^P$, parametrized as $x_2$, and perform a second maximization based on this. The additional component $s_5^P$ can be obtained by measuring a specific observable that we denote $T_2$ $T_2$ is here different from $T_1$. It should be noted that the maximizations should be done independently, i.e., if $s_4$ is to be investigated $s_5$ should be removed and vice versa.

The result of each of the performed maximizations is a number specifying the potential, i.e., the highest probability, that a measurement of $T_1$ or T2 would determine the correct biological condition causing the biological symptoms $s_1$, $s_2$ and $s_3$. By comparing the result of the different maximizations one is able to select the biological test that yields the largest probability of determining the biological condition. If, for example, the method yields that the maximization with regard to $x_1$ is larger than the maximization with regard to $x_2$, one should select the biological test associated with $x_1$ as the next biological step. That is, performing a measurement of observable $T_1$.

The optimization steps, including for example the maximization of (*) and (**) above may be done in several well-known ways. One may for example use a random search algorithm. Such an algorithm works as follows:
1. Start at a random point in search space.
2. Create a sphere around the chosen point
3. Sample a random point in the sphere and evaluate the function at the selected point.
4. If the function value has improved move to the new sampled point and go to step 2, otherwise go to step 3.
5. Continue this procedure until an iteration limit is reached or an adequate result is obtained.

One may also use a so called particle swarm optimization. Initially a set (swarm) of points (particles) are randomly sampled in the search space. The points (particles) are then moved around in the search space by following a set of rules. The movement of a point (particle) will depend on its own best known position and the set's (swarms) best known position. This is a well-known procedure for optimizing expressions as in (*) and (**).

Still another possible evaluation method is the Nelder-Mead algorithm. This works schematically in the following way. Let at first the input to the objective function consist of n variables. Create a simplex with n+1 vertices in the search space. Apply a sequence of transformation to the simplex in order to obtain better function values at the vertices. The transformations should be selected by sampling additional test points.

The above briefly described methods are all well-known for a person skilled in the art of optimizing. Other alternatives utilizes gradient based optimization methods. These are also well known in the art. The proposed technology provides a novel gradient based alternative that is suitable for the problem at hand, i.e., to select biological tests to be performed on a biological subject in order to determine the biological condition of the biological subject. This alternative will be described in greater detail later in this disclosure.

To further clarify the workings of the proposed technology, let us apply it to select an additional test to be performed on a patient in order to increase the confidentiality that the patient suffers from appendicitis. Note that this is merely an example of how the method may be used and also note that the provided parameters are strictly made up in order to facilitate the understanding of the proposed technology.

At first we specify the biological symptoms $s_1$ and $s_2$ that form the input data to the method. Assume that measurements performed on the patient, or information obtained from the patient, yields that the patient suffers from stomach pains and high temperature. For example temperature T=39.2 and an approximation of the pain level 7 on a scale of 1-10, where 1 means no pain at all. This information may be represented as s'=[39.2, 10, 0, 0 . . . 0]$^+$ in a created basis representation s. Suppose further that we have decided to check whether appendicitis or pancreatitis is the biological condition causing the symptoms. To this end let us specify that the predictive model yielded the probability distribution d as:

$$d=[d_1,d_2]^+,$$

where $d_1$ denotes the probability that appendicitis is causing the problems and $d_2$ that pancreatitis is causing the symptoms. Assume further that an observable can be parametrized as $x_1$, and another observable can be parametrized by $x_2$. Suppose that we want to check how the probability $d_1$ will change when the vector is supplemented with $x_1$ and $x_2$. This particular problem formulation will use an optimization in the shape of a maximization, that is, we want to evaluate the following expressions:

$$\max d_1([39.2,10,x_1,0]^+) \text{ with respect to } x_1 \quad (*)$$

and $$\max d_1([39.2,10,0,x_2]^+) \text{ with respect to } x_2 \quad (**)$$

By using any of the earlier described algorithms these expressions can be evaluated. Suppose for example that the maximization of (*) yields a larger value than the maximization of (**), in order to avoid performing unnecessary tests we should therefore first chose to perform a test associated with the test indicating parameter $x_1$.

Consider for example the case where initially $d_1$ ([39.2, 10, 0, 0])=0.7. If $x_1$ is to be considered relevant for selecting the biological test, $d_1$ should increase when $x_1$ is measured. Assume now that max $d_1$ ([39.2, 10, $x_1$, 0]$^+$)=0.9, we see here that $d_1$ increased and that a biological test associated with $x_1$ is a good choice for increasing the confidentiality that the biological condition is associated with $d_1$. Correspondingly we may evaluate max $d_1$ ([39.2, 10, 0, $x_2$]$^+$) to obtain, e.g., 0.7, that is, a biological test associated with $x_2$ would be meaningless since there is no change in $d_1$. Consequently one should choose a biological test associated with the parameter $x_1$.

The above examples were clearly highly simplified and illustrated in a very specific setting. It should be noted that the method may be applied to any complex biological system, it may for example be used to determine suitable tests to be performed on plants, cells, etc., in order to determine the biological condition of the same. The relevant feature of such complex systems are that they have observables that can be measured or probed and that there is sufficient information comprised in a data base that enables the determination of a predictive model M(s) by applying a neural network.

It should also be noted that the steps S5 and S6 of the proposed method may be generalized in such a way that the additional, or second, optimization—either a maximization or a minimization—is done with regard to an arbitrary number N of test indication, i.e., that the following is done:

$$\text{Max or Min } d_i([s_1^P,s_2^P,s_3^P,x_1,0 \ldots 0]^+) \text{ with respect to } x_1 \quad (*)$$

$$\text{Max or Min } d_i([s_1^P,s_2^P,s_3^P,0,x_2 \ldots 0]^+) \text{ with respect to } x_2 \quad (**)$$

$$\text{Max or Min } d_i([s_1^P,s_2^P,s_3^P,0,0,x_3 \ldots 0]^+) \text{ with respect to } x_3 \quad (**)$$

etc., up to $$\text{Max or Min } d_i([s_1^P,s_2^P,s_3^P,0,0, \ldots x_N]^+) \text{ with respect to } x_N.$$

The result of the various optimization—either maximization or minimization—should be compared and a biological test should be selected based on the comparison. If for example max $d_i$ ([$s_1^P$, $s_2^P$, $s_3^P$, 0, 0, $x_3$ . . . 0]$^+$) yielded the largest value one should select a biological test associated with $x_3$ as the next test.

Having described the various steps performed by the proposed computer-implemented method we will now proceed and describe various embodiments and examples of the method.

According to a particular embodiment of the proposed technology there is provided a computer implemented method wherein the number of biological symptoms $s_i$, $1 \le i \le N$, experienced by the biological subject comprises at least two different biological symptoms $s_1$ and $s_2$.

According to another particular embodiment of the proposed technology there is provided a computer-implemented method, wherein the basis representation s of a set of biological symptoms $s_i$ comprises a vector representation where the components of the vector provides information about a specific biological symptom.

According to yet another particular embodiment of the proposed technology there is provided a computer-implemented method, wherein the basis representation s of a set of biological symptoms $s_i$ comprises a vector representation where the vector representation further comprises vector components that provides additional information about a specific biological symptom, the information comprising for example the duration and intensity of a specific biological symptom.

The particular vector representation of the above embodiment may perhaps best be understood by reference to a particular example. Consider the following table:

TABLE 2

| Biological symptoms and additional information | | |
|---|---|---|
| Symptom | First dimension | Second dimension |
| $s_1$ | Parameter $s_{11}$ | Parameter $s_{12}$ |
| $s_2$ | Parameter $s_{21}$ | Parameter $s_{22}$ |
| $s_3$ | Parameter $s_{31}$ | Parameter $s_{32}$ |

The table above describes how particular symptoms $s_i$, i=1, 2, 3, can be parametrised by utilizing two connected but distinct parameters $s_{i1}$ and $s_{i2}$. The two indices may be seen as a collective index that specify both a symptom and the additional information. A particular basis representation of the table above may be provided by a vector representation s that can be written as:

$$s=[s_{11},s_{12},s_{21},s_{22},s_{31},s_{32}]^+ \quad (***)$$

The first dimension may refer to a specific biological state while the second dimension may refer to some additional information about the state that cannot be extracted by merely knowing the biological state. The following table provides a more concrete example of how additional information about a biological symptom can be used:

TABLE 3

| Biological symptoms and additional information | | |
|---|---|---|
| Symptom | First dimension | Second dimension |
| $s_1$ = Fever | $s_{11}$ = Temperature above 38° C. | $s_{12}$ = Duration of temperature above 38° |

TABLE 3-continued

Biological symptoms and additional information

| Symptom | First dimension | Second dimension |
|---|---|---|
| $s_2$ = Stomach pain | $s_{21}$ = Binary input 0 or 1 | $s_{22}$ = Pain intensity given by pain level from 0-10 |
| $s_3$ = Vomiting | $s_{31}$ = Binary input yes or no | $s_{32}$ = Time elapsed since last incidence |

This data can be represented by inserting the parameters into the representation given by (***) above. The data may then be subjected to the predictive model M (s) in order to obtain a probability distribution or probability vector. The additional information will improve the significance of the outcome from the predictive model M(s).

According to particular version of the proposed technology there is provided a computer-implemented method, wherein the input data further comprises, for each of the biological symptoms $s_i$, at least one additional parameter, the additional parameter providing additional information about the nature of the symptoms, and wherein the step of generating a representation s' of the input data in the created basis representation s comprises to represent the input data in a vector representation having a first set of components that provides information about specific biological symptoms and a second set of components that provides additional information about at least some of the specific biological symptoms.

According to another particular embodiment of the proposed technology there is provided a computer-implemented method, wherein the additional information comprises the duration and intensity of a specific biological symptom.

We will now provide an additional example that illustrates how a minimization of a probability $d_i$ comprised in the probability distribution d may be used to select a suitable biological test to be performed on a biological subject.

Assume that we have a data base that comprises information that correctly correlates the biological state of a biological subject based on different biological symptoms. Without loss of generality we will specify to the example where the biological subject is a patient, the biological symptoms are health related symptoms and the biological state is a diagnosis. Assume further that we have recorded, e.g., measured or obtained in some other fashion, symptoms of specific patient. To avoid being to general we specify the example by the inserted variables in table 4 below:

TABLE 3

Biological symptoms and additional information

| Symptom | First dimension | Second dimension |
|---|---|---|
| $s_1$ = Fever | $s_{11}$ = Body temperature | $s_{12}$ = Duration of high body temperature |
| $s_2$ = Stomach ache | $s_{21}$ = Binary input 0 or 1 | $s_{22}$ = Pain intensity given by pain level from 0-10 |
| $s_3$ = Rashes | $s_{31}$ = Binary input yes or no | $s_{32}$ = Estimated coverage from 0 to 1 |

Based on the variables in Table 4 we are able to create a vector representation s that can be written as:

$$s=[s_{11},s_{12},s_{21},s_{22},s_{31},s_{32}]^+ \quad (***)$$

The first dimension thus refer to the presence of a specific symptom while the second dimension refer to additional information related to the corresponding symptom, that is additional information about the symptom that cannot be extracted by merely knowing that the patient displayed the symptom.

Suppose now that we consider three possible diagnosis that are the underlying cause of the symptoms carried by the patient. Let us for example consider the case where the first diagnosis is labeled A, the second diagnosis is labeled B and the third diagnosis is labeled C. This information can be collected in the vector:

$$d=[d_1,d_2,d_3]^+,$$

where $d_1$ is the probability that the true diagnosis is A, $d_2$ is the probability that the true diagnosis is B and $d_3$ is the probability that the true diagnosis is C. Assume that a data base such as the one represented in Table 1 is used to obtain a predictive model M(s) that can be applied on any S.

If a patient now specifies that she has experienced a body temperature of 40.1° C. for three days this information can be represented as:

$$s'=[40.1,0,0,3,0,0]^+$$

If we now apply the predictive model M(s) on s' we could, as an example, end up with:

$$d=[0.71,0.1,0.19]^+,$$

If we now want to improve our certainty that the patient does not carry C, which for example may be the most serious diagnosis represented in d, we would like to evaluate the following expressions:

$$\text{Min } d_3([40.1,x_1,0,3,x_2,0]^+), \quad (Z)$$

$$\text{Min } d_3([40.1,0,x_1,3,0,x_2]^+), \quad (W)$$

These expressions may be evaluated by any of the methods proposed herein. Assume that the evaluation of (Z) yields the optimal value for $d_3$=0.12 and that the evaluation of (W) yields the optimal value for $d_3$=0.03, we could therefore conclude that a biological test geared towards finding rashes would increase our confidence in neglecting C as the most probable diagnosis and the recommended test to perform would therefore be a test for finding rashes. Note that this is a made up example that is only intended to illustrate how the proposed method may be used.

According to still another embodiment of the proposed technology there is provided a computer-implemented method, wherein the step S5 of performing a first optimization of a probability $d_i$ comprised in the probability distribution d is comprises to perform the optimization by evaluating the gradient of the probability $d_i$ with respect to a test indicating parameter $x_k$ representing an additional biological symptom sk represented in the basis representation s, and wherein the step S5 of performing at least one additional optimization of the obtained probability $d_i$ comprised in the probability distribution d is performed by evaluating the gradient of the probability $d_i$ with respect to a different test indicating parameter $x_l$, l≠k, representing an additional biological symptom $s_l$ represented in the basis representation s.

In other words, having obtained a d from step S4 of the proposed computer-implemented method, the method proceeds and performs the first and the additional optimizations by using a gradient based method. The outcome of this method is a set of numbers $d_i^*$, $d_i^{}$, $di^{*}$, etc., taking value in the range [0, 1]. The size of the set depends on how many optimizations that were performed in step S6. If a number K of optimizations were performed in S6, then the size of the set will be K+1. The numbers obtained by the optimizations are to be compared in order to select a specific one. There are several ways to design the comparison criterion. The below embodiment provides a particular example of how the comparison can be made in the case where a single additional optimizations is performed. Based on the outcome of the comparison a biological test is to be selected. The biological test is associated with the specific parameter $x_k$ included in the optimization that came out as the best in the comparison.

According to a particular embodiment of the proposed technology there is provided a computer-implemented method, wherein the optimization comprises a maximization and wherein the step of determining a biological test to be conducted on the biological subject based on a comparison between the obtained maximized probability values $d_i^*$, $d_i^{**}$ comprises to select a biological test associated with the test indicating parameter $x_1$, if $d_i^*$ is larger than $d_i^{}$ and select a biological test associated with $x_2$, if $d_i^{}$ is larger than $d_i^*$.

We will now proceed and describe how a gradient based optimization may be done by means of an example. The example illustrates a maximization but work equally well for a minimization.

Assume that a biological condition $d_i$ depends on two biological symptoms or two observables x and y such that $s=[x, y]^+$. Suppose further that the true relationship is given by $$d_i(s)=2x+3y-xy-x^2-y^2. \quad (3)$$

This means that the input is two dimensional and the output is one dimensional. If we now for example define $s_0=[1, -1]^+$, then we can evaluate the expression so that $$d_i(s_0)=-2. \quad (4)$$

The gradient of a function is a vector of the same size as the input. This means that the gradient $\nabla d_i$ is a vector of two elements. Element j of a gradient is the partial derivative of the function with respect to the j:th variable. Thus, in the case at hand, $$\nabla d_i(s)=[2-y-2x, 3-x-2y]^+, \quad (5)$$

and $$\nabla d_i(s_0)=[1,4]^+. \quad (6)$$

The gradient is a measure of how the function increases if small increases are made in the vector describing the biological symptom. For instance, a small increase in y would increase $d_i$ more than a small increase in x would do, because 4>1. For this interpretation to be valid it is important that there are small changes in the variables, unless the underlying function is linear. If we would like to make larger changes in the symptom vector we would have to make small changes in steps by recalculating the gradient in each step. A way to maximize $d_i$ from a given start point is to adjust the biological symptoms according to the gradient in steps. The factor of how far you follow the gradient in each step is referred to as the step size. If you want to minimize $d_i$ you instead follow the gradient in the reverse direction. This method is also known as the gradient descent method.

Now be proceed and briefly illustrates how a gradient based method may be applied in order to perform a maximization.

Assume we want to maximize the function in Equation (3) and that our current position is given by $s_0$ such that the current gradient is given by the one in Equation (6). Let us now adjust the position by taking a step in the gradient direction. Additionally let the step size be ⅓. Our new point is thus given by:

$$s_1=s_0+⅓\nabla d_i(s_0)=[4/3,⅓]^+. \quad (8)$$

With the updated position one obtains $$d_i(s_1)=⅓ \quad (9)$$

and, $$\nabla d_i(s_1)=[-1,1]^+. \quad (7)$$

The objective function has thus increased its value but the gradient tells us that this can be improved by decreasing x and increasing y. We therefore take an additional step along the gradient. Let $$s_2=s_1+⅓\nabla d_i(s_1)=[1,⅔] \quad (8)$$

This yields, $$d_i(s_2)=17/9 \quad (9)$$

This is yet again an improvement. The process will in the present example stop at $$s_9=[⅓,⅓]^+$$

where the gradient becomes zero, i.e., $\nabla d_i(s_9)=[0, 0]$. In this position the function will not increase in any direction which is known as a local optima. Therefore $s_9$ is a solution to the maximization of d(s).

We will now proceed and describe a particularly suitable embodiment of the proposed technology. This embodiment enables a swift and reliable determination of a biological test to be conducted on a biological subject in order to determine the biological condition of the biological subject.

To this end define the following two weight matrices:

$$W_h = \begin{bmatrix} w^h_{1,1} & \cdots & w^h_{1,n_s} \\ \vdots & \ddots & \vdots \\ w^h_{n_h,1} & \cdots & w^h_{n_h,n_s} \end{bmatrix}, W_o = \begin{bmatrix} w^o_{1,1} & \cdots & w^o_{1,n_h} \\ \vdots & \ddots & \vdots \\ w^h_{n_d,1} & \cdots & w^h_{n_d,n_h} \end{bmatrix},$$

and the following two bias vectors:

$$b_h = \begin{bmatrix} b^h_1 \\ \vdots \\ b^h_{n_h} \end{bmatrix}, b_o = \begin{bmatrix} b^o_1 \\ \vdots \\ b^o_{n_d} \end{bmatrix},$$

here $n_h$, $n_d$ and $n_s$ are the number of nodes in the hidden layer of the network, the number of elements in the diagnosis vector and the number of elements in the symptom vector respectively. The weight element $w_{i,j}^h$ is a multiplicative weight from the preprocessed symptom element j to the hidden layer node i. Similarly, the weight element $w_{i,j}^o$ is a multiplicative weight from the hidden layer node j to the output layer node i. The bias element $b_i^h$ is an additive weight to the hidden layer node i. Similarly, the bias element $b_i^o$ is an additive weight to the output layer node i.

The estimated probability distribution over the diagnoses, defined as d(s), is then modeled as an artificial neural network such that $$d(s)=\sigma_{softmax}(W_o(\tan h(W_h g_{minmax}(s)+b_h))+b_o).$$

The softmax function is defined as $$\sigma_{softmax}(x) = \frac{1}{e^{x_1}+\ldots+e^{x_n}} \begin{bmatrix} e^{x_1} \\ \vdots \\ e^{x_n} \end{bmatrix}.$$

The preprocessing function is applied element wise and is defined as $$g_{minmax}(s_i) = \frac{1}{s_{i,max} - s_{i,min}}(2s_i - (s_{i,max} + s_{i,min})),$$

where $s_{i,max}$ and $s_{i,min}$ are the largest and smallest observed value of the parametrization of biological symptom i respectively.

The weights and the biases in the neural network may be determined by minimizing the error on a sub set of the already known sample set. A possible error measure in to use in this this setting is the so-called Cross Entropy. The gradient of the network output with respect to the weights and biases can be calculated by the well-known Backpropagation algorithm.

Given this it is possible to analytically determine the gradient of component i of d(s) with respect to the symptom vector s. It can be shown that $$(\nabla_s \hat{d}_i)^T = -\hat{d}_i \begin{bmatrix} \hat{d}_1 \\ \vdots \\ \hat{d}_i - 1 \\ \vdots \\ \hat{d}_{n_d} \end{bmatrix}^T W_o((1 - a_h \odot a_h) \odot W_h \text{diag}(2\oslash(s_{max} - s_{min}))),$$

where $\nabla_s$ is the gradient with respect to the elements in s. The vector transpose is noted by the elevated T and 1 is a column vector of ones. The output of the hidden layer is defined as:

$$a_h = \tan h(W_h g_{minmax}(s) + b_h).$$

We have used $\odot$ to refer to element wise array multiplication such that $$\begin{bmatrix} x \\ y \end{bmatrix} \odot \begin{bmatrix} x \\ y \end{bmatrix} = \begin{bmatrix} x^2 \\ y^2 \end{bmatrix}, \begin{bmatrix} x \\ y \end{bmatrix} \odot \begin{bmatrix} a & b \\ c & d \end{bmatrix} = \begin{bmatrix} xa & xb \\ yc & yd \end{bmatrix}.$$

The element wise division operator $\oslash$ is defined such that $$1 \oslash \begin{bmatrix} x \\ y \end{bmatrix} = \begin{bmatrix} 1/x \\ 1/y \end{bmatrix}.$$

The function diag(s) creates a matrix such that the input vector becomes the diagonal, e.g.

$$\text{diag}\left(\begin{bmatrix} x \\ y \end{bmatrix}\right) = \begin{bmatrix} x & 0 \\ 0 & y \end{bmatrix}.$$

It is thus possible to perform the evaluation of the optimization in steps S5 and S6 of the proposed method by utilizing a gradient based method where the gradient is obtained by evaluating the expression:

$$(\nabla_s \hat{d}_i)^T = -\hat{d}_i \begin{bmatrix} \hat{d}_1 \\ \vdots \\ \hat{d}_i - 1 \\ \vdots \\ \hat{d}_{n_d} \end{bmatrix}^T W_o((1 - a_h \odot a_h) \odot W_h \text{diag}(2\oslash(s_{max} - s_{min}))),$$

A particular version of the computer-implemented method according to the proposed technology provides a method wherein the biological symptoms comprises symptoms indicating a disease or a bodily dysfunctionality of the biological subject and wherein the biological condition comprises a diagnosis of the biological subject.

According to yet another particular embodiment of the computer-implemented method there is provided a method wherein the biological subject is an animal or a human.

According still another specific embodiment of the computer-implemented method there is provided a method wherein the biological subject is a plant or a cell.

Having described various embodiments of the proposed computer-implemented method we will now proceed and describe various systems that are configured to perform the proposed method. To this end reference will be made to the drawings where similar reference numerals refers to similar components. The particular benefits and advantages obtained by specific embodiments has been described earlier in relation to the computer-implemented method. These benefits and advantages are equally valid for the proposed system and will not be repeated.

It will be appreciated that the methods and arrangements described herein can be implemented, combined and re-arranged in a variety of ways.

For example, embodiments may be implemented in hardware, or in software for execution by suitable processing circuitry, or a combination thereof.

The steps, functions, procedures, modules and/or blocks described herein may be implemented in hardware using any conventional technology, such as discrete circuit or integrated circuit technology, including both general-purpose electronic circuitry and application-specific circuitry.

Alternatively, or as a complement, at least some of the steps, functions, procedures, modules and/or blocks described herein may be implemented in software such as a computer program for execution by suitable processing circuitry such as one or more processors or processing units.

Examples of processing circuitry includes, but is not limited to, one or more microprocessors, one or more Digital Signal Processors (DSPs), one or more Central Processing Units (CPUs), video acceleration hardware, and/or any suitable programmable logic circuitry such as one or more Field Programmable Gate Arrays (FPGAs), or one or more Programmable Logic Controllers (PLCs).

It should also be understood that it may be possible to re-use the general processing capabilities of any conventional device or unit in which the proposed technology is implemented. It may also be possible to re-use existing software, e.g. by reprogramming of the existing software or by adding new software components.

According to an aspect of the proposed technology there is provided a system configured to determine a biological test to be performed on a biological subject in order to determine the biological condition of the biological subject. The system is configured to create a basis representation s for a set of biological symptoms. The system is also configured to read input data obtained from a biological subject whose biological condition is to be determined, the input data comprising parameters quantifying a number of biological symptom $s_i$, $1 \leq i \leq N$ associated with the biological subject. The system is also configured to generate a representation s' of the input data in the created basis representation s. The system is also configured to apply a predictive model M(s) to the representation s' of the input data in order to obtain a probability distribution d that yields the probabilities $d_i$ that the parameters comprised in the input data corresponds to a specific biological condition $y_j$, the predictive model M(s) being determined by applying a neural network on a set of data, the set of data comprising collected empirical data associating the biological symptoms $s_i$ with a determined biological condition $y_j$. The system is also configured to perform a first optimization of a probability $d_i$ comprised in the probability distribution d with respect to a test indicating parameter $x_1$, the test indicating parameter $x_1$ being associated with a biological symptom $s_k$ different from the biological symptoms $s_i$, and being represented in the basis representation s, in order to obtain a first optimized probability value $d_i^*$. The system is also configured to perform at least one additional optimization of the obtained probability $d_i$ comprised in the probability distribution d with respect to a different test indicating parameter $x_2$, the test indicating parameter $x_2$ being associated with yet another additional biological symptom $s_m$ different from the additional biological symptom $s_k$ and the biological symptom $s_i$, and being represented in the basis representation s, in order to obtain at least one additional optimized probability value $d_i^{**}$. The system is also configured to determine a biological test to be conducted on the biological subject based on a comparison between the obtained optimized probability values $d_i^*$, $d_i^{**}$.

Figure 2:
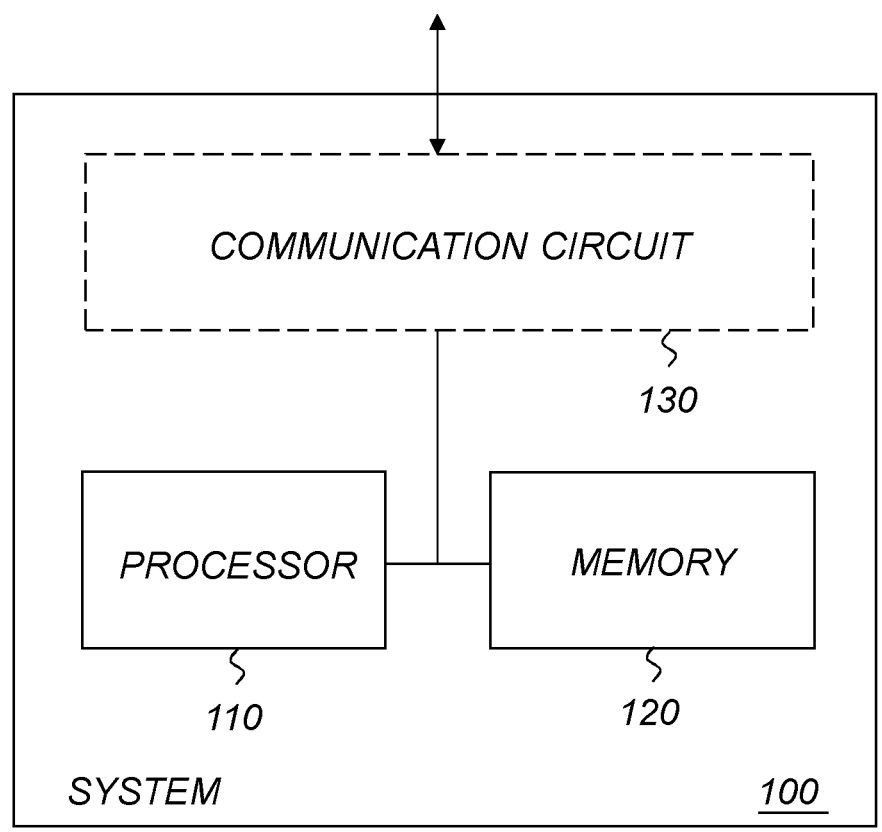
FIG. 2 is a schematic block diagram illustrating a particular embodiment of a system according to the proposed technology.

FIG. 2 is a schematic block diagram illustrating an example of a system 100, based on a processor-memory implementation according to an embodiment. In this particular example, system 100 comprises a processor 110 and a memory 120, the memory 120 comprising instructions executable by the processor 110, whereby the processor is operative to:
  create a basis representation s for a set of biological symptoms;
  read input data obtained from a biological subject whose biological condition is to be determined, the input data comprising parameters quantifying a number of biological symptom $s_i$, $1 \le i \le N$, associated with the biological subject,
  generate a representation s' of the input data in the created basis representation s;
  apply a predictive model M(s) to the representation s' of the input data in order to obtain a probability distribution d that yields the probabilities $d_i$ that the parameters comprised in the input data corresponds to a specific biological condition $y_j$, the predictive model M(s) being determined by applying a neural network on a set of data, the set of data comprising collected empirical data associating the biological symptoms $s_i$ with a determined biological condition $y_j$,
  perform a first optimization of a probability $d_i$ comprised in the probability distribution d with respect to a test indicating parameter $x_1$, the test indicating parameter $x_1$ being associated with a biological symptom $s_k$ different from the biological symptoms $s_i$, and being represented in the basis representation s, in order to obtain a first optimized probability value $d_i^*$
  perform at least one additional optimization of the obtained probability $d_i$ comprised in the probability distribution d with respect to a different test indicating parameter $x_2$, the test indicating parameter $x_2$ being associated with yet another additional biological symptom $s_m$ different from the additional biological symptom $s_k$ and the biological symptom $s_i$, and being represented in the basis representation s, in order to obtain at least one additional optimized probability value $d_i^{**}$, and
  determine a biological test to be conducted on the biological subject based on a comparison between the obtained optimized probability values $d_i^*$, $d_i^{**}$.

Figure 3:
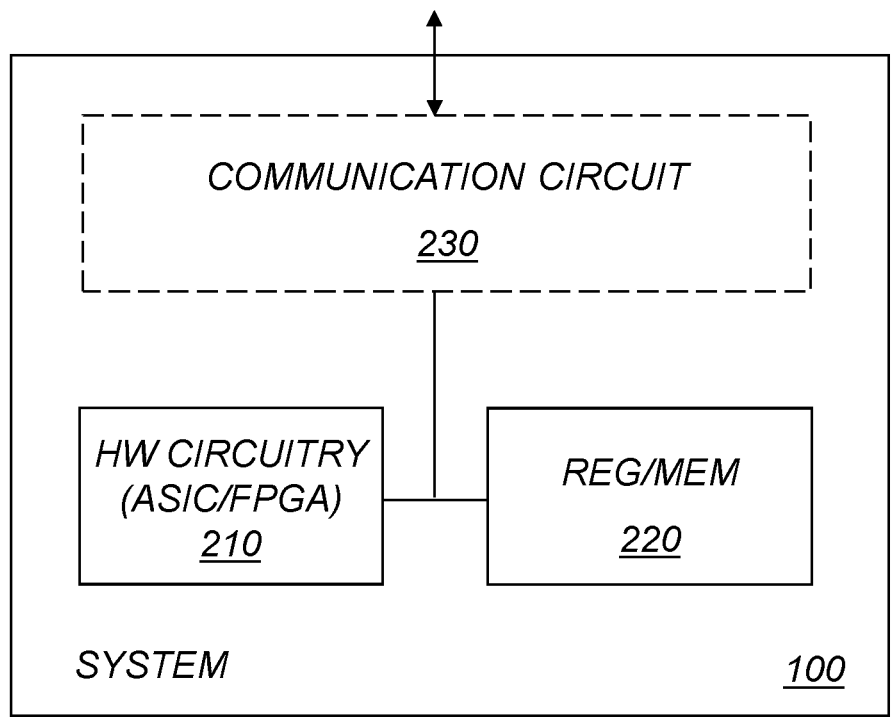
FIG. 3 is a schematic block diagram illustrating an alternative embodiment of a system according to the proposed technology.

FIG. 3 is a schematic block diagram illustrating another example of a system 100, based on a hardware circuitry implementation according to an embodiment. Particular examples of suitable hardware circuitry 210 include one or more suitably configured or possibly reconfigurable electronic circuitry, e.g. Application Specific Integrated Circuits (ASICs), Field Programmable Gate Arrays (FPGAs), or any other hardware logic such as circuits based on discrete logic gates and/or flip-flops interconnected to perform specialized functions in connection with suitable registers (REG) and/or memory units (MEM) 220.

Optionally, the system 100; may also include a communication circuit 130; 230. The communication circuit 130; 230 may include functions for wired and/or wireless communication with other devices. The communication circuit is in a particular example configured to communicate with an external neural network that applies the predictive model M(s) on the created representation s'. The communication circuit 130; 230 may for example be based on radio circuitry for communication with one or more other devices, including transmitting and/or receiving information. The communication circuit 130 may be interconnected to the processor 110 and/or memory 120. The communication circuit 230 may be interconnected to the hardware circuitry 210 and/or REG/MEM 220. By way of example, the communication circuit 130; 230 may include any of the following: a receiver, a transmitter, a transceiver, input/output (I/O) circuitry, input port(s) and/or output port(s). The input/output circuitry may comprise a user interface that enables the input of the read data obtained from a biological subject whose biological condition is to be determined and the output of e.g., the determined biological test.

It is also possible to provide a solution based on a combination of hardware and software. The actual hardware-software partitioning can be decided by a system designer based on a number of factors including processing speed, cost of implementation and other requirements.

A particular embodiment of the proposed technology provides a system wherein the number of biological symptom $s_i$, $1 \le i \le N$, experienced by the biological subject comprises at least two different biological symptoms $s_1$ and $s_2$ experienced by the biological subject.

According to another embodiment of the proposed technology there is provided a system, wherein the basis representation s of a set of biological symptoms $s_i$ comprises a vector representation where the components of the vector provides information about a specific biological symptom.

Still another embodiment of the proposed technology provides a system wherein the input data further comprises, for each of the biological symptoms $s_i$, at least one additional parameter, the additional parameter providing additional information about the nature of the symptoms, and wherein the system is configured to generate a representation s' of the input data in the created basis representation s by representing the input data in a vector representation having a first set of components that provides information about specific biological symptoms and a second set of components that provides additional information about at least some of the specific biological symptoms.

By way of example, the proposed technology provides an embodiment of a system wherein the additional information comprises the duration and/or the intensity of a specific biological symptom.

A particular embodiment of the proposed technology provides a system that is configured to perform the first optimization of a probability $d_i$ comprised in the probability distribution d by evaluating the gradient of the probability $d_i$ with respect to a test indicating parameter $x_i$ representing an additional biological symptom $s_3$ represented in the basis representation s. The system is also configured to perform at least one additional optimization of the obtained probability $d_i$ comprised in the probability distribution d by evaluating the gradient of the probability $d_i$ with respect to a different test indicating parameter $x_j$, $j \neq i$, representing an additional biological symptom $s_4$ represented in the basis representation s.

According to a particular embodiment of the proposed technology there is provided a system 100, wherein the first optimization comprises a maximization, and wherein the at least one additional optimization comprises maximizations.

The proposed technology also provides a system 100 wherein the first optimization comprises a maximization and the at least one additional optimization comprises maximizations and wherein the step of determining a biological test to be conducted on the biological subject based on a comparison between the obtained maximized probability values $d_i^*$, $d_i^{**}$ comprises to select a biological test associated with symptom $x_1$, if $d_i^*$ is larger than $d_i^{}$ and select a biological test associated with $x_2$, if $d_i^{}$ is larger than $d_i^*$.

According to a particular embodiment of the proposed technology there is provided a system 100 wherein the biological symptoms comprises symptoms indicating a disease or a bodily dysfunctionality of the biological subject and wherein the biological condition comprises a diagnosis of the biological subject.

A specific embodiment of the proposed technology provides a system 100 wherein the biological subject is an animal or a human.

A possible embodiment of the proposed technology provides a system that comprises at least one processor 110 and a memory 120, the memory 120 comprising instructions executable by the at least one processor 110, whereby the at least one processor is operative to determine a biological test to be performed on a biological subject in order to determine the biological condition of the biological subject.

It is also possible to provide a solution based on a combination of hardware and software. The actual hardware-software partitioning can be decided by a system designer based on a number of factors including processing speed, cost of implementation and other requirements.

Figure 4:
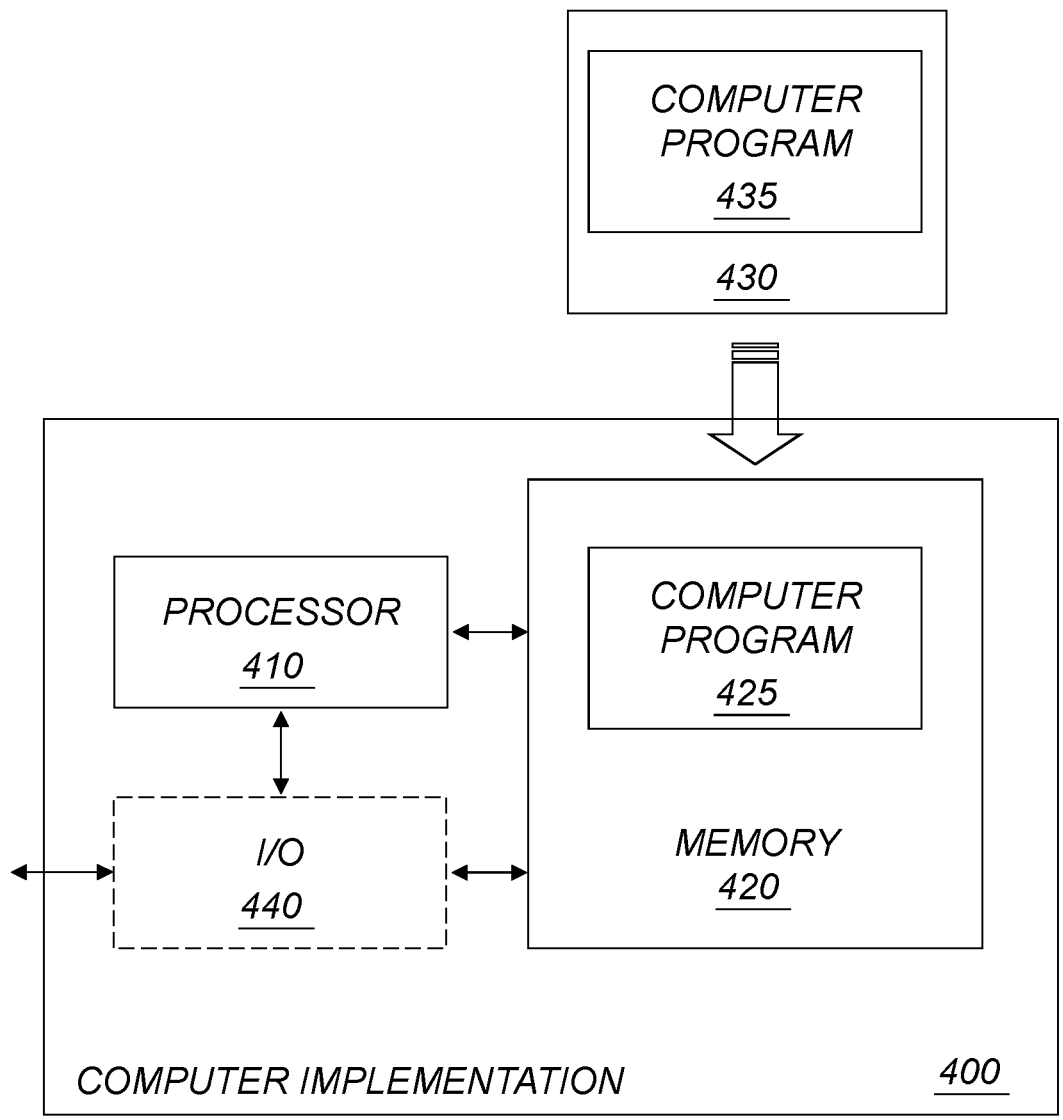
FIG. 4 is a schematic block diagram illustrating a computer-implementation according to the proposed technology.

FIG. 4 is a schematic diagram illustrating an example of a computer-implementation 400 according to an embodiment. In this particular example, at least some of the steps, functions, procedures, modules and/or blocks described herein are implemented in a computer program 425; 435, which is loaded into the memory 420 for execution by processing circuitry including one or more processors 410. The processor(s) 410 and memory 420 are interconnected to each other to enable normal software execution. An optional input/output device 440 may also be interconnected to the processor(s) 410 and/or the memory 420 to enable input and/or output of relevant data such as input parameter(s) and/or resulting output parameter(s).

The term 'processor' should in the present disclosure be interpreted in a general sense as any system or device capable of executing program code or computer program instructions to perform a particular processing, determining or computing task.

The processing circuitry including one or more processors 410 is thus configured to perform, when executing the computer program 425, well-defined processing tasks such as those described herein.

The processing circuitry does not have to be dedicated to only execute the above-described steps, functions, procedure and/or blocks, but may also execute other tasks.

In a particular embodiment, the computer program 425; 435 comprises instructions, which when executed by at least one processor 410, cause the processor(s) 410 to:
- create a basis representation s for a set of biological symptoms;
- read input data obtained from a biological subject whose biological condition is to be determined, the input data comprising parameters quantifying a number of biological symptom $s_i$, $1 \leq i \leq N$, associated with the biological subject;
- generate a representation s' of the input data in the created basis representation s;
- read a probability distribution d that yields the probabilities $d_i$ that the parameters comprised in the input data corresponds to a specific biological condition $y_j$, the probability distribution d being obtained by applying a predictive model M(s) to the representation s' of the input data, the predictive model M(s) being determined by applying a neural network on a set of data, the set of data comprising collected empirical data associating the biological symptoms $s_i$ with a determined biological condition $y_j$;
- perform a first optimization of a probability $d_i$ comprised in the probability distribution d with respect to a test indicating parameter $x_1$, the test indicating parameter $x_1$ being associated with a biological symptom $s_k$ different from the biological symptoms $s_i$, and being represented in the basis representation s, in order to obtain a first optimized probability value $d_i^*$;
- perform at least one additional optimization of the obtained probability $d_i$ comprised in the probability distribution d with respect to a different test indicating parameter $x_2$, the test indicating parameter $x_2$ being associated with yet another additional biological symptom $s_m$ different from the additional biological symptom $s_k$ and the biological symptom $s_i$, and being represented in the basis representation s, in order to obtain at least one additional optimized probability value $d_i^{**}$; and
- output a specific biological test to be conducted on the biological subject, the biological test being determined based on a comparison between the obtained optimized probability values $d_i^*$, $d_i^{**}$.

The proposed technology also provides a carrier comprising the computer program, wherein the carrier is one of an electronic signal, an optical signal, an electromagnetic signal, a magnetic signal, an electric signal, a radio signal, a microwave signal, or a computer-readable storage medium.

By way of example, the software or computer program 425; 435 may be realized as a computer program product, which is normally carried or stored on a computer-readable medium 420; 430, in particular a non-volatile medium. The computer-readable medium may include one or more removable or non-removable memory devices including, but not limited to a Read-Only Memory (ROM), a Random Access Memory (RAM), a Compact Disc (CD), a Digital Versatile Disc (DVD), a Blu-ray disc, a Universal Serial Bus (USB) memory, a Hard Disk Drive (HDD) storage device, a flash memory, a magnetic tape, or any other conventional memory device. The computer program may thus be loaded into the operating memory of a computer or equivalent processing device for execution by the processing circuitry thereof.

APPENDIX

Artificial Neural Networks or Neural Networks

In this appendix we will briefly explain artificial neural networks, ANN, or just simply NN for short and how they can be used to obtain a predictive model M(s). It is a computing system that is to some degree inspired by the biological neural network that makes up a brain. Mathematically speaking it can be viewed as a nonlinear parametric regression model. The basic idea is that the elements of the input to the network is altered with weights and biases and sent through summation nodes and transfer functions to finally reach the output. The weights and biases are then optimized iteratively to reduce the error on the data set, this step is called training. The programming can for example be done in Matlab with the help of the Neural Network Toolbox™. But other possibilities exist.

Data Pre-Processing

It is often good practice to pre-process the data by scaling it before using it for learning. This is to avoid the problem of some features with large numerical values and variance having un-proportionally large impact on the model. Scaling the features can also improve the convergence of gradient descent methods. Imagine we have observed values of an unscaled feature x and that we wish to scale it to x^. One technique of achieving this is to do the following: subtract the mean $\overline{x}$ and divide by the standard deviation $\sigma_x$ for that feature to obtain $\hat{x}_{std}$. Another common technique is to map the largest value of the feature $x_{max}$ to 1 and the smallest $x_{min}$ to −1 and do linear interpolation on the points in between to obtain $\hat{x}_{minmax}$. Let g(x) be a general scaling function given by:

$$g_{minmax}(s_i) = \frac{1}{s_{i,max} - s_{i,min}}(2s_i - (s_{i,max} + s_{i,min})),$$

Before training the same scaling method may be applied to all of the features separately in the data set. It is also preferable to remove features that are constant over all samples because they do not provide any new information and may slow down the optimization. For instance, biological subjects such as patients may have been asked to give a perceived pain level in their left hand. If all patients in the data set gives the same answer, e.g., no pain, that feature becomes useless because you cannot tell what happens if a change is made in that feature by looking at the data set. It may become useful in the future when more data is collected and if the network is retrained on this new data set and the feature is not constant anymore it will not be removed this time.

From Input to Output

A general neural network can be divided into four parts: inputs, hidden layers, output layers and outputs. These parts can be combined and used in a very large number of ways but the NNs we will consider will consist of one input, one hidden layer, one output layer and one output. We will also limit the flow of information to only be forward also known as feedforward networks. We will therefore consider what is known as single layer feedforward artificial neural networks. Let the input to the network be denoted by s. The first step is to apply the pre-processing element wise on the input to obtain s'=g(s). This vector is then sent to the so called hidden layer consisting of $n_h$ summation nodes. What this means mathematically is that s^ which in our case is of length $2n_v$ is transformed into $s_h$ of length $n_h$ in the following way:

$$s_h = W^\wedge{}_h s' + b_h,$$

where $W_h$ is a weight matrix of size $n_h \times 2n_v$ and $b_h$ is a bias vector of length $n_h$. Choosing the right amount of nodes in the hidden layer is a complex task. A sometimes useful rule of thumb for a starting point is to use a number between the input and output size, i.e. $n_d \leq n_h \leq 2n_v$ but in practice it depends e.g., on the hidden layer transfer function and the size of the training set. A hidden layer transfer function $\sigma_h(\bullet)$ may then be applied element wise to $s_h$ to obtain $a_h$. Some examples of transfer functions are:

$$\sigma_{tan\ h(x)} = 2/(1+e^{-2x})-1 = \tan h(x),$$

$$\sigma_{log\ sig(x)} = 1/(1+e^{-x})$$

$$\sigma_{purelin(x)} = x.$$

Typically the transfer function is selected to be sigmoid which intuitively is seen as an "S"-shaped curve. Formally a sigmoid function is a bounded, differentiable and real function with non-negative derivative globally. The purpose of the transfer function is generally to introduce nonlinearity to the model so that it may describe nonlinear patterns. The output from the hidden layer is formulated as $a_h = \sigma_h(s_h)$. This vector is then sent to the output layer. The output layer has to have $n_d$ summation nodes because that is the length of the desired output of the network. This means that an is transformed into $s_0$ of length $n_d$ in the following way:

$$s_0 = W_0 a_h + b_0,$$

where $W_0$ is a weight matrix of size $n_d \times n_h$ and $b_0$ is a bias vector of length $n_d$. Finally an output transfer function $\sigma_0(\frown)$ is applied to so to obtain the output d of the network.

The whole network can be summarized into:

$$d(s) = \sigma_{softmax}(W_p(\tan h((W_h g_{minmax}(s) + b_h)) + b_o).$$

We now see that the network can be viewed as a somewhat complicated nonlinear regression model of the form d=f (s). The model parameters are the elements in $W_h$, $b_h$, $W_0$ and $b_0$. These add up to a total of $n_h$ $(2n_v + n_d + 1) + n_d$ parameters. For instance if we have 7 symptoms and 5 biological conditions and apply the previously stated rule of thumb we obtain about 125 regression parameters.

Training the Network

Finding the optimal values for the model parameters is generally a rather complex high dimensional Non-Linear problem, NLP. In practice one might have to accept approximate local optimality. Initially the parameters may be randomized and the error on the training set is calculated. The gradient of the error with respect to the weights may be calculated using a method called backpropagation. That gradient is then used in an optimization algorithm called scaled conjugate gradient that determines the locally optimal direction to adjust the weights in. The weights may then be adjusted in and a new direction calculated. If the step is sufficiently small the performance is improved in each step. When any out of a set of conditions is met the algorithm stops. Some of the conditions are iteration limit, time limit and if the performance on the validation set has not improved over multiple iterations.

Avoiding Overfitting

When the number of model parameters in a regression model increases the error on the training set decreases. This is so because the introduction of more parameters increases the flexibility of the function thus allowing it to follow the data points more closely. Consider for instance a simple linear model. If we in this model introduce as many parameters as observations we can solve for the parameters and thereby obtain an exact fit. This may however not be the general pattern since the function may follow random errors in the data set. If we however use too few parameters the model will have bad accuracy. Overfitting in a neural network is often avoided by limiting the number of hidden layer neurons and by introducing a validation set. Generally the data set is randomly divided into the 3 following parts 1. Training set. This set typically contains 70% of the observations. The performance is optimized over this set iteratively.

2. Validation set. This set typically contains 15% of the observations. An error is calculated but not optimized over this set. If the error on the validation set has not improved over 5 iterations the optimization stops. This is to avoid overfitting the training set.

3. Test set. This set typically contains 15% of the observations. When the optimization is complete the overall performance is calculated on unseen samples that is the test set. This is to get a measure on how well the network will perform on new data. If the error on the test set is considerably larger than the error on the training set it is likely that overfitting has occurred and that the number of nodes in the hidden layer may have to be reduced. It is recommended to retrain the network without the test set afterwards to increase the precision of the network, therefore the reported test error is likely an overestimate.

Finding Optimal Network Properties

There is a lot of decisions to make when designing a neural network such as hidden and output layer transfer functions, the number of neuron in the hidden layer, how to randomize weights initially, pre-processing function, error definition and training algorithm. One way of determining the optimal choice of something, say hidden layer transfer function, is to keep all others things constant and calculate the averaged test performance over multiple runs and see how it changes when the transfer function is changed. The reason why an average is useful is because the weights are initially randomized and the partitioning of the data set is randomized so the performance will fluctuate between runs even if no design choice has changed.

The invention claimed is:

1. A biological analysis support system configured to provide support for analyzing a biological system based on biological measurement data, said biological analysis support system comprising:

an input configured to receive input data obtained based on biological measurements from a biological subject whose biological condition is to be determined, said input data comprising parameters quantifying a number of biological symptoms $s_i$, $1 \leq i \leq N$, associated with said biological subject, wherein the measurements enable parametrization of biological symptoms associated with the measurements;

processing circuitry configured to:

create a basis representation s for a set of said biological symptoms;

generate a representation s' of said input data in said created basis representation S;

apply a predictive model M(s) to said representation s' of said input data in order to obtain a probability distribution d that yields the probabilities $d_i$ that said parameters comprised in said input data corresponds to a specific biological condition yj, said predictive model M(s) being determined by applying a neural network on a set of data, said set of data comprising collected empirical data associating said biological symptoms s, with a determined biological condition $y_j$;

perform a first optimization of a probability $d_i$ comprised in said probability distribution d with respect to a test indicating parameter $x_1$, said test indicating parameter $x_1$ being associated with a biological symptom $s_k$ different from said biological symptoms $s_i$, and being represented in said basis representation s, in order to obtain a first optimized probability value $d_i^*$;

perform at least one additional optimization of said obtained probability $d_i$ comprised in said probability distribution d with respect to a different test indicating parameter $x_2$, said test indicating parameter $x_2$ being associated with yet another additional biological symptom $s_m$ different from said additional biological symptom $s_k$ and said biological symptom $s_i$, and being represented in said basis representation s, in order to obtain at least one additional optimized probability value $d_i^{**}$; and determine a specific biological test to be conducted on said biological subject based on a comparison between said obtained optimized probability values $d_i^*$, $d_i^{**}$, and an output for outputting output data representative of said specific biological test to be conducted on said biological subject, thereby enabling a reduction of the number of conducted tests, which in turn reduces the strain on the biological subject and reduces time and costs associated with the analysis of the biological system.

2. The system according to claim 1, wherein said number of biological symptom $s_i$, $1 \leq i \leq N$, experienced by said biological subject comprises at least two different biological symptoms $s_1$ and $s_2$ experienced by said biological subject.

3. The system according to claim 1, wherein said basis representation s of a set of biological symptoms s, comprises a vector representation where the components of said vector provides information about a specific biological symptom.

4. The system according to claim 3, wherein said input data further comprises, for each of said biological symptoms $s_i$, at least one additional parameter, said additional parameter providing additional information about the nature of said symptoms, and wherein the system is configured to generate a representation s' of said input data in said created basis representation s by representing said input data in a vector representation having a first set of components that provides information about specific biological symptoms and a second set of components that provides additional information about at least some of said specific biological symptoms.

5. The system according to claim 4, wherein said additional information comprises the duration and/or the intensity of a specific biological symptom.

6. A system for providing computer-implemented support for analyzing biological systems and for determining an upcoming measurements procedure by determining a biological test to be performed on a biological subject in order to determine the biological condition of the biological subject, wherein the system comprises at least one processor and memory, the memory comprising instructions, which when executed by the at least one processor, cause the at least one processor to:

create a basis representation s for a set of biological symptoms;

read input data obtained, based on measurements, from a biological subject whose biological condition is to be determined, said input data comprising parameters quantifying a number of biological symptoms $s_i$, $1 \le i \le N$, associated with said biological subject, wherein the measurements enable parametrization of biological symptoms associated with the measurements;

generate a representation s' of said input data in said created basis representation s;

apply a predictive model M(s) to said representation s' of said input data in order to obtain a probability distribution d that yields the probabilities $d_i$ that said parameters comprised in said input data corresponds to a specific biological condition $y_j$, said predictive model M(s) being determined by applying a neural network on a set of data, said set of data comprising collected empirical data associating said biological symptoms s, with a determined biological condition $y_j$;

perform a first optimization of a probability $d_i$ comprised in said probability distribution d with respect to a test indicating parameter $x_1$, said test indicating parameter $x_1$ being associated with a biological symptom $s_k$ different from said biological symptoms $s_i$, and being represented in said basis representation s, in order to obtain a first optimized probability value $d_i^*$;

perform at least one additional optimization of said obtained probability $d_i$ comprised in said probability distribution d with respect to a different test indicating parameter $x_2$, said test indicating parameter $x_2$ being associated with yet another additional biological symptom $s_m$ different from said additional biological symptom $s_k$ and said biological symptom $s_i$, and being represented in said basis representation s, in order to obtain at least one additional optimized probability value $d_i^{**}$; and determine a biological test to be conducted on said biological subject based on a comparison between said obtained optimized probability values $d_i^*$, $d_i^{**}$, and output data representative of said biological test to be conducted on the biological subject, thereby enabling a reduction of the number of conducted tests, which in turn reduces the strain on the biological subject and reduces time and costs associated with the analysis of the biological system.

7. The system according to claim 6, wherein said number of biological symptom $s_i$, $1 \le i \le N$, experienced by said biological subject comprises at least two different biological symptoms $s_1$ and $s_2$ experienced by said biological subject.

8. The system according to claim 6, wherein said basis representation s of a set of biological symptoms s, comprises a vector representation where the components of said vector provides information about a specific biological symptom.

9. The system according to claim 8, wherein said input data further comprises, for each of said biological symptoms $s_i$, at least one additional parameter, said additional parameter providing additional information about the nature of said symptoms, and wherein the system is configured to generate a representation s' of said input data in said created basis representation s by representing said input data in a vector representation having a first set of components that provides information about specific biological symptoms and a second set of components that provides additional information about at least some of said specific biological symptoms.

10. The system according to claim 9, wherein said additional information comprises the duration and/or the intensity of a specific biological symptom.

11. The system according to claim 6, wherein said first optimization comprises a maximization, and wherein said at least one additional optimization comprises maximizations.

12. The system according to claim 6, wherein said first optimization comprises a maximization and said at least one additional optimization comprises maximizations and wherein the system is configured to perform said first maximization of a probability $d_i$ comprised in said probability distribution d by evaluating the gradient of the probability $d_i$ with respect to a test indicating parameter x, representing an additional biological symptom $s_3$ represented in said basis representation s, and wherein the system is configured to perform said at least one additional maximization of said obtained probability $d_i$ comprised in said probability distribution d by evaluating the gradient of the probability $d_i$ with respect to a different test indicating parameter $x_1$, $j \ne i$, representing an additional biological symptom $s_4$ represented in said basis representation s.

13. The system according to claim 6, wherein said first optimization comprises a maximization and said at least one additional optimization comprises maximizations and wherein the step of determining a biological test to be conducted on said biological subject based on a comparison between said obtained maximized probability values $d_i^*$, $d_i^{**}$ comprises to select a biological test associated with symptom $x_1$, if $d_i^*$ is larger than $d_i^{}$ and select a biological test associated with $x_2$, if $d_i^{}$ is larger than $di^*$.

14. The system according to claim 6, wherein said biological symptoms comprises symptoms indicating a disease or a bodily dysfunctionality of the biological subject and wherein said biological condition comprises a diagnosis of said biological subject.

15. The system according to claim 14, wherein said biological subject is an animal or a human.

16. A non-transitory computer-readable medium on which a computer program is stored, said computer program comprising instructions, which when executed by at least one processor, cause said at least one processor to:

create a basis representation s for a set of biological symptoms;

read input data obtained, based on measurements, from a biological subject whose biological condition is to be determined, the input data comprising parameters quantifying a number of biological symptoms $s_i$, $1 \le i \le N$, associated with the biological subject, wherein the measurements enable parametrization of biological symptoms associated with the measurements;

generate a representation s' of the input data in the created basis representation s;

read a probability distribution d that yields the probabilities $d_i$ that the parameters comprised in the input data corresponds to a specific biological condition $y_j$, the probability distribution d being obtained by applying a predictive model M(s) to the representation s' of the input data, the predictive model M(s) being determined by applying a neural network on a set of data, the set of data comprising collected empirical data associating the biological symptoms s, with a determined biological condition $y_j$;

perform a first optimization of a probability $d_i$ comprised in the probability distribution d with respect to a test indicating parameter $x_1$, the test indicating parameter $x_1$ being associated with a biological symptom $s_k$ different from the biological symptoms $s_i$, and being represented in the basis representation s, in order to obtain a first optimized probability value di*;

perform at least one additional optimization of the obtained probability $d_i$ comprised in the probability distribution d with respect to a different test indicating parameter $x_2$, the test indicating parameter $x_2$ being associated with yet another additional biological symptom $s_m$ different from the additional biological symptom $s_k$ and the biological symptom $s_i$, and being represented in the basis representation s, in order to obtain at least one additional optimized probability value $d_i^{**}$; and output a specific biological test to be conducted on the biological subject, the biological test being determined based on a comparison between the obtained optimized probability values $d_i^*$, $d_i^{**}$, thereby enabling a reduction of the number of conducted tests, which in turn reduces the strain on the biological subject and reduces time and costs associated with the analysis of the biological system.

* * * * *